United States Patent
Lamberts et al.

(10) Patent No.: US 12,103,901 B2
(45) Date of Patent: Oct. 1, 2024

(54) METHOD FOR PRODUCING A COMPOSITION CONTAINING AT LEAST ONE METAL AMINO ACID COMPOUND AND COMPOSITION OBTAINABLE BY MEANS OF A METHOD OF THIS KIND

(71) Applicant: BIOCHEM Zusatzstoffe Handels- und Produktionsgesellschaft mbH, Lohne (DE)

(72) Inventors: Kevin H. W. Lamberts, Idstein (DE); Ismet Bice, Rastede (DE); Heiko Greimann, Lohne (DE)

(73) Assignee: BIOCHEM Zusatzstoffe Handels- und Produktionsgesellschaft mbH, Lohne (DE)

( * ) Notice: Subject to any disclaimer, the term of this patent is extended or adjusted under 35 U.S.C. 154(b) by 940 days.

(21) Appl. No.: 17/059,275

(22) PCT Filed: Apr. 23, 2019

(86) PCT No.: PCT/EP2019/060351
§ 371 (c)(1),
(2) Date: Nov. 27, 2020

(87) PCT Pub. No.: WO2019/233671
PCT Pub. Date: Dec. 12, 2019

(65) Prior Publication Data
US 2021/0227851 A1      Jul. 29, 2021

(30) Foreign Application Priority Data
Jun. 4, 2018   (DE) .................. 102018113243.3

(51) Int. Cl.
| | | |
|---|---|---|
| C07C 229/76 | (2006.01) |
| A23K 20/142 | (2016.01) |
| A23K 20/20 | (2016.01) |
| C07C 227/16 | (2006.01) |
| C07C 227/38 | (2006.01) |
| C07F 1/08 | (2006.01) |
| C07F 3/06 | (2006.01) |
| C07F 13/00 | (2006.01) |
| C07F 15/02 | (2006.01) |
| A23K 40/00 | (2016.01) |

(52) U.S. Cl.
CPC .......... *C07C 229/76* (2013.01); *A23K 20/142* (2016.05); *A23K 20/30* (2016.05); *C07C 227/16* (2013.01); *C07C 227/38* (2013.01); *C07F 1/08* (2013.01); *C07F 3/06* (2013.01); *C07F 13/005* (2013.01); *C07F 15/025* (2013.01); *A23K 40/00* (2016.05)

(58) Field of Classification Search
CPC ... C07C 227/16; C07C 227/38; C07C 229/76; A61K 31/30; A61K 31/315; A61K 31/295; A61K 33/26; A61K 33/30; A61K 33/32; A61K 33/34; C07F 1/08; C07F 3/06; C07F 13/005; C07F 15/025
See application file for complete search history.

(56) References Cited

U.S. PATENT DOCUMENTS

| | | | |
|---|---|---|---|
| 2,877,253 A | 3/1959 | Rummel | |
| 2,957,806 A | 10/1960 | Rummel | |
| 4,183,947 A | 1/1980 | Cockerill | |
| 4,830,716 A * | 5/1989 | Ashmead | C07C 51/41 556/50 |
| 6,407,138 B1 * | 6/2002 | Ashmead | C07C 227/16 556/50 |
| 6,458,981 B1 | 10/2002 | Ashmead et al. | |
| 6,710,079 B1 | 3/2004 | Ashmead et al. | |
| 2006/0128799 A1 * | 6/2006 | Park | A61P 39/04 514/505 |
| 2012/0231112 A1 | 9/2012 | Wreesmann et al. | |
| 2014/0037960 A1 | 2/2014 | Rambold et al. | |
| 2017/0121351 A1 | 5/2017 | Nawrocki et al. | |

FOREIGN PATENT DOCUMENTS

| | | |
|---|---|---|
| CN | 101503415 X | 8/2009 |
| EP | 1 453 845 | 6/2003 |
| RU | 2549930 | 12/2013 |
| RU | 2671402 | 7/2018 |

* cited by examiner

*Primary Examiner* — Yate' K Cutliff
(74) *Attorney, Agent, or Firm* — Gudrun E. Huckett

(57) ABSTRACT

The invention relates to a method for producing a composition containing at least one metal amino acid compound, in which method—a basic compound of a divalent metal is first reacted together with an alpha amino acid in a molar relationship of one to at least two in water during heating of up to 60° C. to 100° C.,—a reaction equilibrium is awaited,—the reaction solution is then mixed with a water-soluble salt of the same divalent metal at a quantity such that the molar total quantity of the divalent metal from the basic compound of the metal and the metal salt does not exceed the molar quantity of the alpha amino acid,—the metal salt is allowed to completely dissolve,—the reaction solution is then dried thereby obtaining a solid composition.

13 Claims, No Drawings

METHOD FOR PRODUCING A COMPOSITION CONTAINING AT LEAST ONE METAL AMINO ACID COMPOUND AND COMPOSITION OBTAINABLE BY MEANS OF A METHOD OF THIS KIND

BACKGROUND OF THE INVENTION

The invention relates to a process for preparing a composition comprising at least one metal-amino acid compound, to a composition obtainable by a process of this kind and to the use of a composition of this kind.

Specific metal cations are essential to life for organisms, as they perform important functions in proteins and other molecules. An adequate intake of metal cations is therefore essential. When taken orally, the dosage form of metal cations is critical to the effectiveness of absorption. In the foodstuffs and animal feeds sector, metal cations are typically administered in the form of metal-amino acid compounds, since metal cations are better absorbed by the body in this form.

U.S. Pat. No. 2,877,253 describes a therapeutic iron complex prepared from iron (II) sulfate and glycine. In this complex, the amino acid glycine remains in its neutral form, and the complex contains both the iron (II) cation and the sulfate anion. The complex is prepared by reacting iron (II) sulfate and glycine in a 1:1 molar ratio under aqueous conditions at 70° C. and drying the reaction product under reduced pressure. EP 1 453 845 B1 describes similarly prepared metal-amino acid complexes in which a metal sulfate is reacted with glycine under aqueous conditions and the reaction product then dried by means of vacuum drying and adjusted to a specific degree of hydration. An advantage of such compounds is that they can be prepared in almost any ratio of metal to amino acid, since the amino acid, as a neutral ligand, does not need to provide any necessary charge equalization. This allows the cost-efficiency of the amino acid complexes to be readily adjusted. Moreover, the metal-amino acid complexes all have good solubility in water, thus allowing flexible use. However, they are not actual chelates. True chelates of metals with amino acids (characterized by their five-membered ring) require the amino acid to be present in deprotonated form. The amino acid then serves as ligand and anion and is bound to the metal cation via an oxygen atom and a nitrogen atom.

Chelates of metals with amino acids are however ascribed greater effectiveness when taken orally. Metal-amino acid chelates of this kind and the preparation thereof are disclosed for example in U.S. Pat. No. 6,458,981 B1. They are prepared by reacting the amino acid and a metal salt with calcium hydroxide or calcium oxide in an aqueous medium. The reaction products formed are true metal-amino acid chelates having a five-membered ring, plus calcium sulfate. A disadvantage of this process is that the calcium sulfate formed as a by-product needs to be removed at extra expense or else remains in the product as a reduction in quality.

US 20140037960 A1 describes the preparation of metal-amino acid chelates in which a basic compound of a divalent metal is reacted with glycine in a 1:2 stoichiometric ratio without addition of water. This results in the formation of a metal-amino acid chelate that should be free of by-products. The problem of the low reactivity of the basic compounds of divalent metals is counteracted by a prior mechanical activation in which the metal compounds are milled into very small particles. A disadvantage of metal-amino acid chelates prepared in this way is that the products have poorer solubility in water than simple amino acid complexes, in addition to which the metal to amino acid ratio of 1:2 is not cost-efficient compared with the metal-amino acid ratio of 1:1 in the simple amino acid complexes. The basic compounds of divalent metals would likewise need to be mechanically activated by milling before the start of the reaction, which is associated with greater costs.

The object of the invention is to provide a process for preparing a composition comprising at least one metal-amino acid compound, a composition obtainable by a process of this kind, in which the abovementioned disadvantages are reduced and the advantages in each case are retained, and for the use of a composition of this kind.

SUMMARY OF THE INVENTION

The invention achieves the object through a process for preparing a composition comprising at least one metal-amino acid compound in which a basic compound of a divalent metal is initially reacted together with an alpha-amino acid in a molar ratio of 1 to at least 2 in water while heating to 60° C. to 100° C., there is a wait until the reaction has reached equilibrium, the reaction solution is then treated with a water-soluble salt of the same divalent metal in an amount such that the molar total amount of the divalent metal from the basic compound of the metal and from the metal salt does not exceed the molar amount of the alpha-amino acid, there is a wait until the metal salt has completely dissolved, the reaction solution is then dried to obtain a solid composition.

The overall reaction proceeds essentially in two steps. In the first step, a basic compound of a divalent metal, i.e. of a metal in the +II oxidation state, is reacted together with at least twice the molar amount of an alpha-amino acid in water while heating to 60° C. to 100° C. This results in the formation of a metal-amino acid bis-chelate. The basic compound of the divalent metal initially dissolves, with deprotonation of the amino acid in water; the divalent metal cation thereby released then reacts with two deprotonated amino acids to form a metal-amino acid bis-chelate. The bis-chelate may partly precipitate during the reaction. Depending on the nature of the basic compound of the divalent metal, the reaction may proceed to completion if the basic compound of the metal dissolves completely in water in the presence of the amino acid, or else the dissolution of the basic metal compound stalls, or else the basic metal compound dissolves only to the same degree as fresh basic metal compound is formed in the reverse reaction. However, in all three cases it is necessary to wait until the reaction has reached equilibrium, since reaching equilibrium may mean that the reaction has proceeded to completion. In the second part of the reaction, a water-soluble salt of the same divalent metal is added to the reaction solution in an amount such that the molar total amount of the divalent metal from the basic compound of the metal and from the metal salt does not exceed the molar amount of the alpha-amino acid. The additional metal cations react here with the metal-amino acid bis-chelate that is present, to form one or more complexes. Drying the solution affords a solid composition having a high crystalline fraction, in which the metal-amino acid bis-chelate has combined with the additional metal ions to form a water-soluble product that has a low amino acid content and is free of contaminating by-products.

The process according to the invention allows the molar ratio of metal to amino acid to be set at 1:1. This ratio is particularly cost-efficient, since amino acids are relatively costly by comparison with metal salts, consequently the amino acid content of the composition needs to be kept low in order for the product to be cost-efficient. Conversely, for each metal cation there should be at least one amino acid molecule present in the product, since it is this that ensures the beneficial effect of the amino acid on the absorption of the metal by the body. The product moreover has good solubility in water and the process does not give rise to any unwanted by-products that would need to be removed from the composition at extra expense or else would remain in the composition as an interfering impurity.

In a preferred embodiment of the invention, the basic compound of the divalent metal is a hydroxide, carbonate, hydroxide carbonate or an oxide. On dissolution of the basic metal compounds, the oxide reacts to form water, the hydroxide to form water and the carbonate to form carbonic acid, which is evolved in the reaction in the form of carbon dioxide. The use of basic compounds ensures that the amino acids are present in deprotonated form, thus resulting in the formation of the desired chelates.

It is advantageous when the divalent metal is copper, manganese, zinc or iron. In a preferred embodiment of the invention, the anion of the metal salt is sulfate.

The alpha-amino acid is preferably a naturally occurring, proteinogenic amino acid, particularly preferably glycine or alanine. In a preferred embodiment of the invention, the drying of the reaction solution is carried out in a spray granulator (spray granulation) by fluid-bed drying, this being particularly preferably carried out at a product temperature of 70 to 130° C. and/or in an oven, in a vacuum dryer and/or by spray drying.

The process according to the invention results in the formation of a solid composition having a high crystalline fraction, in which metal cations are presumably bound to the initially formed metal-amino acid bis-chelate to form a new chelate.

The process is assumed to involve the reaction steps shown below. A point to note here is that in each case it is not just the depicted trans-variants of the products that are formed, but possibly also the cis-variants or both together.

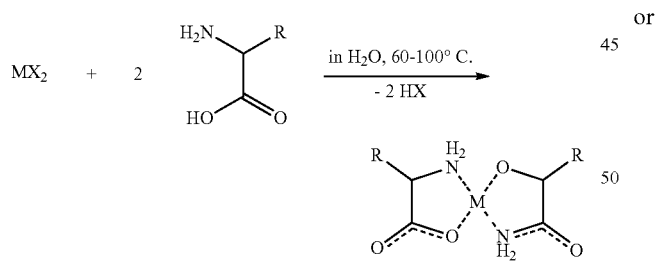

M=divalent metal, X=e.g. OH⁻, R=e.g. H→glycine or CH₃→alanine

Alternatively

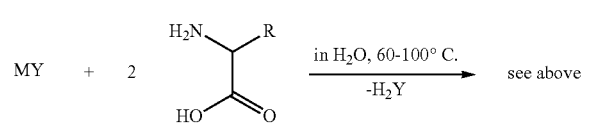

Y=e.g. $CO_3^{2-}$

Further presumed reactions:

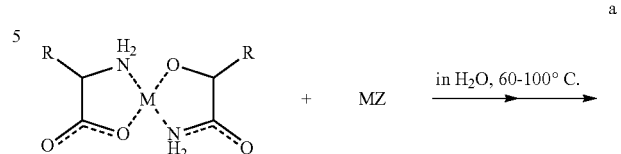

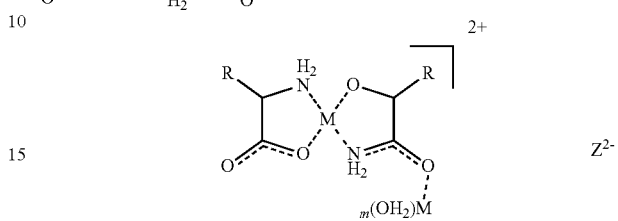

or

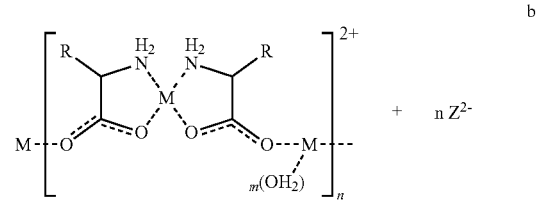

or

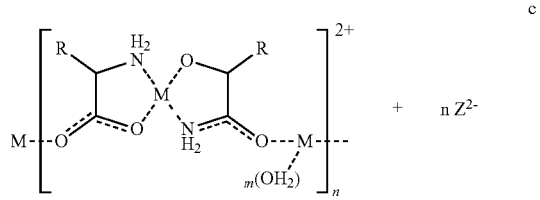

or

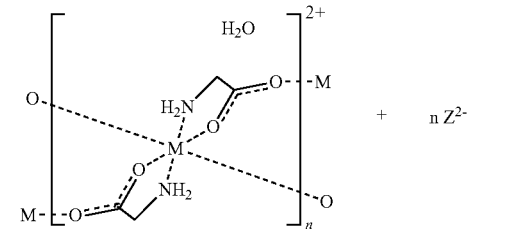

Z=anion of the soluble metal, e.g. $SO_4^{2-}$

BRIEF DESCRIPTION OF THE DRAWINGS

FIG. 1 shows a light microscope image of the product according to Example.

FIG. 2 shows an X-ray powder diffractogram of the product of Example 1 measured by using CuKα₂ irradiation.

FIG. 3 shows an X-ray powder diffractogram of the product of Example 4 measured by using CuKα₂ irradiation.

DESCRIPTION OF PREFERRED EMBODIMENTS

Embodiments of the process according to the invention and of the composition of the invention prepared using a process of this kind are elucidated in more detail below.

The composition comprising at least one metal-amino acid compound obtained by the method according to the invention can be used for enriching animal feeds with divalent metals of high bioavailability.

Example 1

418 g of basic copper carbonate ($Cu_2CO_3(OH)_2H_2O$) is added, with stirring, to 4.5 kg of water. 600 g of glycine ($NH_2CH_2COOH$) is then added, with stirring, and the suspension is boiled for 40 minutes. This results in the dissolution of the turquoise-green basic copper carbonate, with evolution of gas and the formation of a dark blue solution with a precipitate of the same colour. 624 g of copper sulfate pentahydrate ($CuSO_4 \cdot 5H_2O$) is then added, with stirring, to the hot reaction and the mixture is boiled for a further 10 minutes. A dark blue clear solution forms, which was dried into a granulate by spray granulation in a fluid bed using a Glatt GPCG 3.1 dryer operated with the following parameters:

| Air inflow | 140-150° C. | Air inflow rate: | 50-90 m³/h |
|---|---|---|---|
| Air outflow | 75-85° C. | Product | 90-110° C. |

The dark blue crystalline and granular composition (FIG. 1) had a copper content of approx. 308 g/kg, a nitrogen content of approx. 83 g/kg and a surface water content of approx. 54 g/kg. It is characterized by an X-ray powder diffractogram (FIG. 2) that for Cu-K$\alpha_1$ irradiation at room temperature has particularly characteristic reflections at 11.99, 13.37, 19.39, 20.03, 21.60, 22.55, 23.09, 28.37, 29.81, 30.63 and 31.23° at 2θ.

Example 2

17 kg of basic copper carbonate ($Cu_2CO_3(OH)_2H_2O$) is added, with stirring, to 150 kg of water. 24.3 kg of glycine ($NH_2CH_2COOH$) is then added, with stirring, and the suspension is boiled for 30 minutes. This results in the dissolution of the turquoise-green basic copper carbonate, with evolution of gas and the formation of a dark blue solution with a precipitate of the same colour. 25.25 kg of copper sulfate pentahydrate ($CuSO_4 \cdot 5H_2O$) is then added, with stirring, to the hot reaction and the mixture is boiled for a further 15 minutes. A dark blue clear solution forms, which was dried into a granulate by spray granulation in a fluid bed using a Glatt AGT 400 dryer operated with the following parameters:

| Air inflow temperature: | 180-220° C. | Air inflow rate: | 1000-1200 m³/h |
|---|---|---|---|
| Air outflow temperature: | 90-105° C. | Product temperature: | 95-110° C. |

The dark blue crystalline and granular composition had a copper content of approx. 312 g/kg, a nitrogen content of approx. 84 g/kg and a surface water content of approx. 12.2 g/kg. It is characterized by an X-ray powder diffractogram that for Cu-K$\alpha_1$ irradiation at room temperature has particularly characteristic reflections at 10.29, 11.67, 13.27, 14.84, 16.32, 19.15, 20.23, 22.29, 23.76, 27.47, 28.01, 29.12, 31.47 and 33.42 at 2θ.

Example 3

680 kg of basic copper carbonate ($Cu_2CO_3(OH)_2H_2O$) is added, with stirring, to 4000 kg of water. 972 kg of glycine ($NH_2CH_2COOH$) is then added, with stirring, and the suspension is boiled for 30 minutes. This results in the dissolution of the turquoise-green basic copper carbonate, with evolution of gas and the formation of a dark blue solution with a precipitate of the same colour. 1010 kg of copper sulfate pentahydrate ($CuSO_4 \cdot 5H_2O$) is then added, with stirring, to the hot reaction and the mixture is boiled for a further 15 minutes. A dark blue clear solution forms, which was dried into a granulate by spray granulation in a fluid bed using a Glatt AGT 2200 dryer operated with the following parameters:

| Air inflow temperature: | 170-190° C. | Air inflow rate: | 40 000-45 000 m³/h |
|---|---|---|---|
| Air outflow temperature: | 65-90° C. | Product temperature: | 70-95° C. |

The dark blue crystalline and granular composition had a copper content of approx. 306 g/kg, a nitrogen content of approx. 84.6 g/kg and a surface water content of approx. 32 g/kg. It is characterized by an X-ray powder diffractogram that for Cu-K$\alpha_1$ irradiation at room temperature has particularly characteristic reflections at 10.54, 11.83, 13.27, 15.95, 16.42, 19.10, 20.27, 22.34, 23.83, 27.52, 28.12, 29.23, 31.59, 33.39 at 2θ.

The measurements were in each case carried out using a STADI P powder diffractometer from Stoe & Cie, Darmstadt, in Guinier geometry between films as a flat preparation. The radiation source used was a Cu anode (40 kV, 20 mA) with Cu-Kai irradiation (1.54059 angstroms) generated using a Johann-type germanium monochromator. The detector used was an Imageplate IP-PSD from Stoe & Cie.

None of the compositions mentioned above or compounds obtained from such a composition are present in the relevant crystal structure databases such as the Cambridge Structural Database (CSD).

The following reaction cascade with steps A) and B) is in each case assumed, it not being known exactly which end products or end product composition are formed:

A) Reaction of glycine with basic copper carbonate [$CuCO_3 \cdot Cu(OH)_2$]:

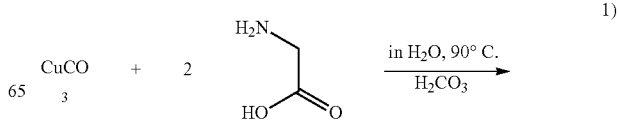

1)

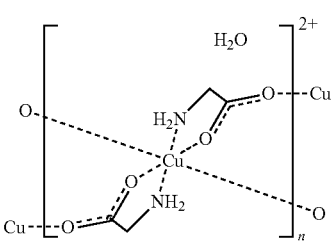

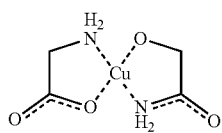

where $H_2CO_3 \rightleftharpoons H_2O + CO_2\uparrow$

2)

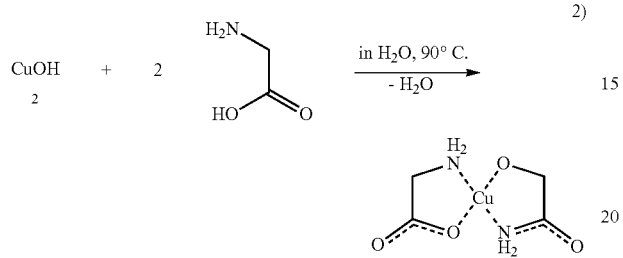

B) Presumed further reactions:

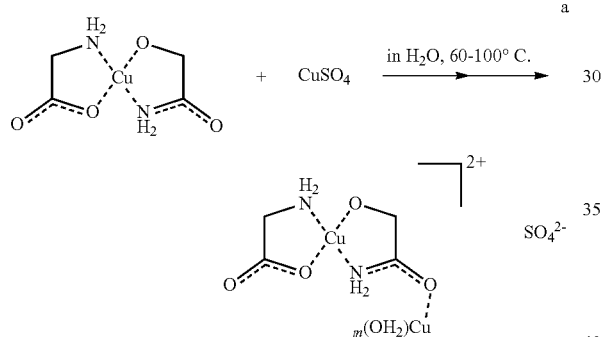

a or

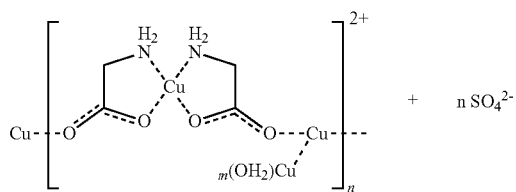

b or

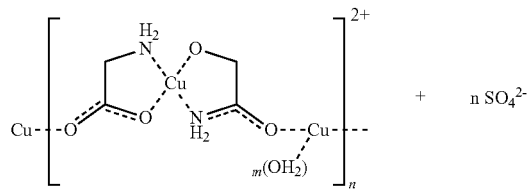

c d

Example 4

268 g of basic zinc carbonate ($Zn_2CO_3(OH)_2H_2O$) is added, with stirring, to 2 kg of water. 336 g of glycine ($NH_2CH_2COOH$) is then added, with stirring, and the suspension is boiled for 40 minutes. This results in the dissolution of the white basic zinc carbonate, with evolution of gas and the formation again of a white suspension. 401 g of zinc sulfate monohydrate ($ZnSO_4 \cdot 1H_2O$) is then added, with stirring, to the hot reaction and the mixture is boiled for a further 10 minutes. A light grey clear solution forms, which was dried into a white granulate by spray granulation in a fluid bed using a Glatt AGT 400 dryer operated with the following parameters:

| Air inflow temperature: | 190-220° C. | Air inflow rate: | 1000-1300 m³/h |
| Air outflow temperature: | 110-125° C. | Product temperature: | 110-130° C. |

The white crystalline composition has a zinc content of approx. 308 g/kg, a nitrogen content of approx. 69 g/kg and a surface water content of less than 5 g/kg. It is characterized by an X-ray powder diffractogram that for Cu-K$\alpha_1$ irradiation at room temperature has particularly characteristic reflections at 7.58, 10.21, 11.67, 15.14, 16.08, 17.53, 18.39, 18.81, 20.54, 20.81, 21.27 and 21.72° at 2θ (FIG. 3).

There is likewise no composition or compound of this kind present in the relevant crystal structure databases such as the Cambridge Structural Database (CSD). The reaction is here presumed to proceed via a cascade analogous to the reaction cascade described above with basic copper carbonate.

What is claimed is:

1. A method for preparing a composition comprising at least one metal-amino acid compound, the method comprising:

carrying out a reaction of a basic compound of a divalent metal with an alpha-amino acid in a molar ratio of 1 to at least 2 in water while heating to 60° C. to 100° C.;

waiting until the reaction has reached an equilibrium, wherein the equilibrium is reached, depending on a nature of the basic compound of the divalent metal, when the basic compound of the divalent metal is dissolved completely in water in the presence of the alpha-amino acid, or when dissolving of the basic metal compound of the divalent metal stalls, or when the basic metal compound of the divalent metal dissolves only to such a degree as fresh basic metal compound of the divalent metal is formed in a reverse reaction;

adding to a reaction solution of the reaction a water-soluble metal salt of the divalent metal in an amount such that a molar total amount of the divalent metal of the basic compound of the divalent metal and of the metal salt of the divalent metal does not exceed a molar amount of the alpha-amino acid;

waiting until the water-soluble metal salt of the divalent metal has completely dissolved in the reaction solution;

drying the reaction solution to obtain the composition as a solid.

2. The method according to claim 1, further comprising the step of selecting the basic compound of the divalent metal from the group consisting of a hydroxide, a carbonate, a hydroxide carbonate, and an oxide.

3. The method according to claim 1, further comprising the step of selecting the divalent metal from the group consisting of copper, manganese, zinc, and iron.

4. The method according to claim 1, wherein an anion of the water-soluble metal salt of the divalent metal is sulfate.

5. The method according to claim 1, wherein the alpha-amino acid is a naturally occurring, proteinogenic amino acid.

6. The method according to claim 1, wherein the alpha-amino acid is glycine.

7. The method according to claim 1, wherein drying of the reaction solution is carried out by one or more methods selected from the group consisting of fluid-bed drying in a spray granulator; oven drying; vacuum drying; and spray drying.

8. The method according to claim 7, wherein fluid-bed drying in a spray granulator is carried out at a product temperature of 70 to 130° C.

9. A composition comprising at least one metal-amino acid compound, the composition obtained as a solid by the method of claim 1.

10. The composition according to claim 9, wherein the basic compound of the divalent metal is a copper compound, wherein the alpha-amino acid is glycine, and wherein the water-soluble metal salt of the divalent metal is a copper sulfate, wherein the composition obtained as the solid is characterized through an X-ray diffractogram obtained by Cu-Kα, irradiation at room temperature and comprising characteristic reflections at 11.99, 13.37, 19.39, 20.03, 21.60, 22.55, 23.09, 28.37, 29.81, 30.63 and 31.23° at 2θ.

11. The composition according to claim 9, wherein the basic compound of the divalent metal is a copper compound, wherein the alpha-amino acid is glycine, and wherein the water-soluble metal salt of the divalent metal is a copper sulfate, wherein the composition obtained as the solid is characterized through an X-ray diffractogram obtained by Cu-Kα, irradiation at room temperature and comprising characteristic reflections at 10.54, 11.83, 13.27, 15.95, 16.42, 19.10, 20.27, 22.34, 23.83, 27.52, 28.12, 29.23, 31.59 and 33.39° at 2θ.

12. The composition according to claim 9, wherein the basic compound of the divalent metal is a copper compound, wherein the alpha-amino acid is glycine, and wherein the water-soluble metal salt of the divalent metal is a copper sulfate, wherein the composition obtained as the solid is characterized through an X-ray diffractogram obtained by Cu-Kα, irradiation at room temperature and comprising characteristic reflections at 10.29, 11.67, 13.27, 14.84, 16.32, 19.15, 20.23, 22.29, 23.76, 27.47, 28.01, 29.12, 31.47 and 33.42° at 2θ.

13. The composition according to claim 9, wherein the basic compound of the divalent metal is a zinc compound, wherein the alpha-amino acid is glycine, and wherein the water-soluble metal salt of the divalent metal is a zinc sulfate, wherein the composition obtained as the solid is characterized through an X-ray diffractogram obtained by Cu-Kα, irradiation at room temperature and comprising characteristic reflections at 7.58, 10.21, 11.67, 15.14, 16.08, 17.53, 18.39, 18.81, 20.54, 20.81, 21.27 and 21.72° at 2θ.

* * * * *